US010864355B2

(12) United States Patent
Root et al.

(10) Patent No.: US 10,864,355 B2
(45) Date of Patent: Dec. 15, 2020

(54) PERFUSION CATHETERS AND RELATED METHODS

(71) Applicant: Teleflex Life Sciences Limited, Valletta (MT)

(72) Inventors: Howard C. Root, Excelsior, MN (US); Chad Kugler, Buffalo, MN (US); Dean Peterson, Minneapolis, MN (US); Joshua Brenizer, Maple Grove, MN (US)

(73) Assignee: Teleflex Life Sciences Limited, Valletta (MT)

( * ) Notice: Subject to any disclaimer, the term of this patent is extended or adjusted under 35 U.S.C. 154(b) by 121 days.

(21) Appl. No.: 16/191,833

(22) Filed: Nov. 15, 2018

(65) Prior Publication Data

US 2019/0083760 A1    Mar. 21, 2019

Related U.S. Application Data

(63) Continuation of application No. 14/850,095, filed on Sep. 10, 2015, now Pat. No. 10,159,821.

(Continued)

(51) Int. Cl.
*A61M 25/10* (2013.01)
*A61B 17/12* (2006.01)
*A61B 17/22* (2006.01)

(52) U.S. Cl.
CPC ..... *A61M 25/1002* (2013.01); *A61B 17/1204* (2013.01); *A61B 17/12036* (2013.01);
(Continued)

(58) Field of Classification Search
CPC ............ A61M 25/1002; A61M 25/104; A61B 17/12036; A61B 17/1204; A61B 17/12109; A61B 17/12136
See application file for complete search history.

(56) References Cited

U.S. PATENT DOCUMENTS 4,762,130 A    8/1988    Fogarty et al.
4,909,252 A    3/1990    Goldberger
(Continued)

FOREIGN PATENT DOCUMENTS

EP    3125781 B1    11/2018
EP    3400886        11/2018
(Continued)

OTHER PUBLICATIONS

European Search Report and Search Opinion dated Oct. 12, 2018, in European application EP18177601.4.
(Continued)

*Primary Examiner* — Richard G Louis
(74) *Attorney, Agent, or Firm* — Greg W. Smock; Robert B. Madden

(57) ABSTRACT

This patent document discloses perfusion catheters and related methods for treating complications related to CTO interventions or dilating a vessel occlusion while maintaining a passage through the treated vessel segment. A perfusion catheter can include a balloon formed of an inflatable tube and an elongate shaft having a lumen for providing inflation fluid to, or withdrawing inflation fluid from, the balloon. The inflatable tube can be coiled in a helical manner around a central axis into a series of windings. Adjacent windings can be stacked against and bonded to each other, and an inner surface of the series of windings, when inflated, can define the passage. The elongate shaft can be eccentrically attached to a proximal portion of the balloon and the shaft's lumen can be in fluid communication with the interior of the balloon, specifically the inflatable tube. The inflatable tube can include two different polymer tubes, one slightly smaller than the other.

19 Claims, 6 Drawing Sheets

Related U.S. Application Data

(60) Provisional application No. 62/078,240, filed on Nov. 11, 2014, provisional application No. 62/048,726, filed on Sep. 10, 2014.

(52) U.S. Cl.
CPC .. *A61B 17/12109* (2013.01); *A61B 17/12136* (2013.01); *A61M 25/104* (2013.01); *A61B 2017/22001* (2013.01); *A61B 2017/22051* (2013.01); *A61B 2017/22094* (2013.01); *A61M 2025/1097* (2013.01)

(56) References Cited

U.S. PATENT DOCUMENTS

| | | | |
|---|---|---|---|
| 4,944,745 A | 7/1990 | Sogard et al. | |
| 5,047,045 A * | 9/1991 | Arney | A61M 25/104 604/103.1 |
| 5,087,247 A | 2/1992 | Horn et al. | |
| 5,181,911 A | 1/1993 | Shturman | |
| 5,195,969 A | 3/1993 | Wang et al. | |
| 5,226,888 A | 7/1993 | Arney | |
| 5,226,889 A | 7/1993 | Sheiban | |
| 5,252,159 A | 10/1993 | Arney | |
| 5,257,974 A | 11/1993 | Cox | |
| 5,368,566 A | 11/1994 | Crocker | |
| 5,370,691 A | 12/1994 | Samson | |
| 5,421,826 A | 6/1995 | Crocker et al. | |
| 5,439,445 A | 8/1995 | Kontos | |
| 5,470,314 A | 11/1995 | Walinsky | |
| 5,505,702 A | 4/1996 | Arney | |
| 5,536,250 A | 7/1996 | Klein et al. | |
| 5,545,135 A | 8/1996 | Iacob et al. | |
| 5,549,552 A | 8/1996 | Peters et al. | |
| 5,554,119 A | 9/1996 | Harrison et al. | |
| 5,556,382 A | 9/1996 | Adams | |
| 5,558,642 A | 9/1996 | Schweich et al. | |
| 5,569,184 A | 10/1996 | Crocker et al. | |
| 5,613,948 A | 3/1997 | Avellanet | |
| 5,643,171 A | 7/1997 | Bradshaw et al. | |
| 5,649,978 A | 7/1997 | Samson | |
| 5,690,642 A | 11/1997 | Osborne et al. | |
| 5,716,340 A | 2/1998 | Schweich et al. | |
| 5,720,723 A | 2/1998 | Adams | |
| 5,738,667 A | 4/1998 | Solar | |
| 5,800,450 A | 9/1998 | Lary et al. | |
| 5,855,546 A | 1/1999 | Hastings et al. | |
| 5,879,369 A | 3/1999 | Ishida | |
| 5,882,290 A | 3/1999 | Kume | |
| 5,891,154 A | 4/1999 | Loeffler | |
| 5,961,490 A | 10/1999 | Adams | |
| 6,083,215 A | 7/2000 | Milavetz | |
| 6,110,097 A | 8/2000 | Hastings et al. | |
| 6,187,014 B1 | 2/2001 | Goodin et al. | |
| 6,190,355 B1 | 2/2001 | Hastings | |
| 6,245,040 B1 | 6/2001 | Inderbitzen et al. | |
| 6,361,529 B1 | 3/2002 | Goodin et al. | |
| 6,503,224 B1 | 1/2003 | Forman et al. | |
| 6,506,180 B1 | 1/2003 | Lary | |
| 6,945,957 B2 | 9/2005 | Freyman | |
| 7,147,655 B2 | 12/2006 | Chermoni | |
| 7,563,247 B2 | 7/2009 | Maguire et al. | |
| 8,430,845 B2 | 4/2013 | Wahr et al. | |
| 8,469,925 B2 | 6/2013 | Rowe et al. | |
| 8,486,014 B2 | 7/2013 | Kelly et al. | |
| 9,968,763 B2 | 5/2018 | Root et al. | |
| 2003/0032920 A1 | 2/2003 | Wantink | |
| 2003/0040704 A1 | 2/2003 | Dorros et al. | |
| 2003/0120208 A1 | 6/2003 | Houser et al. | |
| 2003/0233068 A1 | 12/2003 | Jayaraman | |
| 2004/0093008 A1* | 5/2004 | Zamore | C08F 226/06 606/194 |
| 2004/0142704 A1 | 7/2004 | Scholz | |
| 2004/0230178 A1 | 11/2004 | Wu | |
| 2005/0075662 A1 | 4/2005 | Pedersen et al. | |
| 2006/0142704 A1 | 6/2006 | Lentz | |
| 2006/0210605 A1 | 9/2006 | Chang et al. | |
| 2008/0200896 A1 | 8/2008 | Shmulewitz et al. | |
| 2009/0105641 A1 | 4/2009 | Nissl | |
| 2011/0009818 A1 | 1/2011 | Goff | |
| 2011/0264039 A1 | 10/2011 | Thielen et al. | |
| 2012/0245520 A1* | 9/2012 | Kelly | A61M 25/1002 604/103.09 |
| 2013/0261729 A1 | 10/2013 | Gillick et al. | |
| 2015/0032148 A1 | 1/2015 | Golan | |
| 2016/0066932 A1 | 3/2016 | Root et al. | |
| 2017/0143355 A1 | 5/2017 | Nicholson et al. | |

FOREIGN PATENT DOCUMENTS

| | | |
|---|---|---|
| JP | H09164191 A | 6/1997 |
| JP | 2002503986 A | 2/2002 |
| JP | 2005230579 A | 9/2005 |
| JP | 2011505918 A | 3/2011 |
| JP | 6097447 B2 | 3/2017 |
| JP | 6326517 B2 | 4/2018 |
| WO | 1993007929 A1 | 4/1993 |
| WO | 1994026206 A1 | 11/1994 |
| WO | 1997032626 A2 | 9/1997 |
| WO | 1998055179 A1 | 12/1998 |
| WO | 2000023139 A1 | 4/2000 |
| WO | 2005027995 A2 | 3/2005 |
| WO | 2012037507 A1 | 3/2012 |
| WO | 2014055547 A1 | 4/2014 |

OTHER PUBLICATIONS

International Search Report dated Nov. 24, 2015, from corresponding PCT application PCT/US2015/049356 filed Sep. 10, 2015.
Written Opinion dated Nov. 24, 2015, from corresponding PCT application PCT/US2015/049356 filed Sep. 10, 2015.

* cited by examiner

PERFUSION CATHETERS AND RELATED METHODS

CLAIM OF PRIORITY

This non-provisional patent document is a continuation application of U.S. Non-Provisional Patent Application Ser. No. 14/850,095, now U.S. Pat. No. 10,159,821, entitled "PERFUSION CATHETERS AND RELATED METHODS" and filed on Sep. 10, 2015, which claims the benefit of priority under 35 U.S.C. § 119(e) to U.S. Provisional Patent Application Ser. No. 62/048,726, entitled "PERFUSION CATHETER" and filed on Sep. 10, 2014, and U.S. Provisional Patent Application Ser. No. 62/078,240, entitled "PERFUSION CATHETERS AND RELATED METHODS" and filed on Nov. 11, 2014, each of which is herein incorporated by reference in its entirety. This patent document relates to U.S. Non-Provisional Application Ser. No. 15/296,183, now U.S. Pat. No. 9,968,763, entitled "PERFUSION CATHETERS AND RELATED METHODS" and filed on Oct. 18, 2016, which is also a continuation application of U.S. Non-Provisional Application Ser. No. 14/850, 095, now U.S. Pat. No. 10,159,821.

TECHNICAL FIELD

This patent document relates to medical devices. More particularly, but not by way of limitation, the patent document relates to catheters and related methods for sealing a vessel perforation or dissection or dilating a vessel occlusion.

BACKGROUND

A severe or chronic total occlusion (CTO) is a vessel blockage that prevents blood flow beyond the occlusion. Chronic total occlusions most often occur in coronary and peripheral arteries and result from atherosclerosis.

A procedure for treating CTOs is percutaneous transluminal angioplasty. During an angioplasty procedure, access to a desired blood vessel is obtained and a guidewire is introduced into the blood vessel. The guidewire is maneuvered into place, including being passed into and through the occlusion, and acts as a guide for positioning a subsequent treatment device used to dilate or otherwise treat the vessel occlusion. The treatment device can be advanced over the guidewire so that its distal portion is positioned within the occlusion. A dilatation balloon at the distal portion of the treatment device can then be inflated to apply radial pressure to the occlusive material and adjacent inner wall portions of the vessel, thereby clearing the occlusion to enable better blood flow.

OVERVIEW

The present inventors recognize that CTOs are one of the most challenging lesion subsets in interventional cardiology to treat due to their established occlusive structure. Complications related to CTO interventions include vessel wall perforation and dissection. If not treated without delay, blood hemorrhaging through the perforation or dissection can lead to death of the patient within minutes.

The present inventors further recognize that sealing of the vessel perforation or dissection using conventional balloon catheters causes complete interruption of blood flow within the damaged vessel while the catheter's balloon is inflated. Keeping the balloon inflated for an extended period can risk damage to bodily regions nourished by the vessel—regions already weakened by insufficient blood supply. For example, prolonged dilations of several minutes may need to be employed to effectively treat a perforation. Yet, most adults are only able to withstand non-perfusion dilation of 30-60 seconds without significant side effects.

The present perfusion catheters can be quickly and easily deployed in a damaged vessel and can provide a passage (or flow lumen) formed upon inflation of its balloon. A perfusion catheter can include a balloon formed of an inflatable tube and an elongate shaft having a lumen for providing inflation fluid to, or withdrawing inflation fluid from, the balloon. The inflatable tube can be coiled in a helical manner around a central axis into a series of windings. Adjacent windings can be stacked against and bonded to each other, and an inner surface of the series of windings, when inflated, can define the passage. The elongate shaft can be eccentrically attached to a proximal portion of the balloon and its lumen can be in fluid communication with the interior of the inflatable tube. The inflatable tube can include two different polymer tubes, one slightly smaller than the other. The smaller, inner tube can be formed from a polymer having sufficient radial stiffness to resist collapse or bursting when exposed to inflation pressures, and the larger, outer tube can be formed from a polymer configured to exhibit adhesive properties when heated.

The present methods for sealing a perforation or dissection or dilating occlusive material can include inserting a guidewire into a blood vessel and advancing the guidewire to or across a treatment site, passing a perfusion catheter over the guidewire until a distal portion of the perfusion catheter is positioned near or within the treatment site, and inflating a balloon of the perfusion catheter. Inflating the balloon can include inflating a series of contacting windings of helically-wound tubing. The balloon, upon inflation, can move from a deflated configuration to an inflation configuration at which an outer surface of the balloon can engage a wall of the blood vessel and an inner surface of the balloon can define a passage. The passage can allow a flow of bodily fluid, such as blood, through the perfusion catheter. Optionally, the method can include passing a treatment device at least partially through the passage.

Objects of the present perfusion catheters and related methods include, among others:
1. Sealing a vessel perforation or dissection by blocking the injury from inside the vessel for an extended period of time while maintaining a sufficient flow of blood trough a treated vessel segment;
2. Dilating a vessel occlusion for an extended period of time while maintaining a sufficient flow of blood through a treated vessel segment; and/or
3. Delivering or receiving one or more treatment devices while sealing a vessel perforation or dissection or dilating a vessel occlusion.

These and other examples and objects of the present perfusion catheters and related methods will be set forth in the following Detailed Description. This Overview is intended to provide non-limiting examples of the present subject matter—it is not intended to provide an exclusive or exhaustive explanation. The Detailed Description below is included to provide further information about the present perfusion catheters and related methods.

BRIEF DESCRIPTION OF THE DRAWINGS

In the drawings, like numerals can be used to describe similar features and components throughout the several views. The drawings illustrate generally, by way of example, but not by way of limitation, embodiments discussed in the present patent document.

Figure 1:
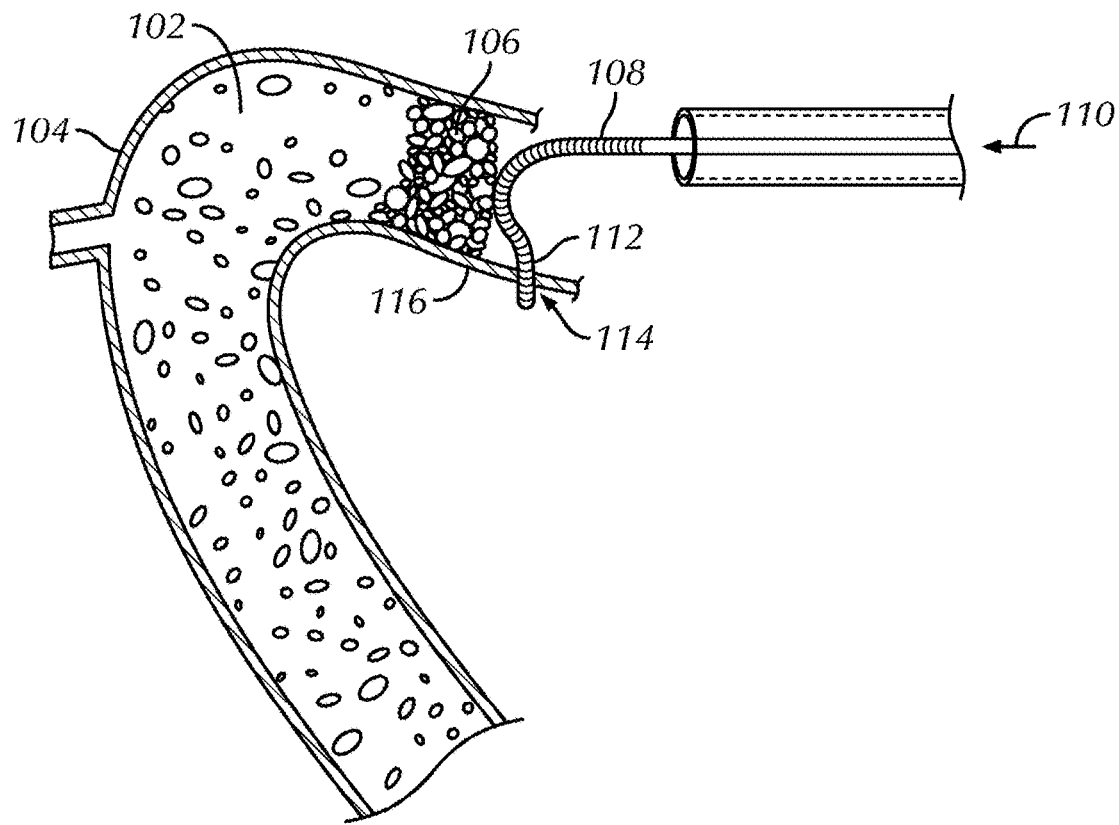
FIG. 1 illustrates a schematic view of a guidewire advanced through a patient's vasculature and unable to penetrate an end cap of an occlusion within a vessel.

The drawing figures are not necessarily to scale. Certain features and components may be shown exaggerated in scale or in schematic form and some details may not be shown in the interest of clarity and conciseness.

DETAILED DESCRIPTION

With the advancement of medical devices and increased training, clinicians are treating CTOs using angioplasty techniques more than ever before. The present catheters and methods provide the clinicians with a means to treat complications related to CTO angioplasty interventions or to dilate a vessel occlusion while maintaining a passage through the treated vessel segment. While the catheters and methods are primarily discussed in relation to treatment of coronary arteries, they may also be useful in other blood vessels throughout the body including peripheral arteries and veins.

Figure 2:
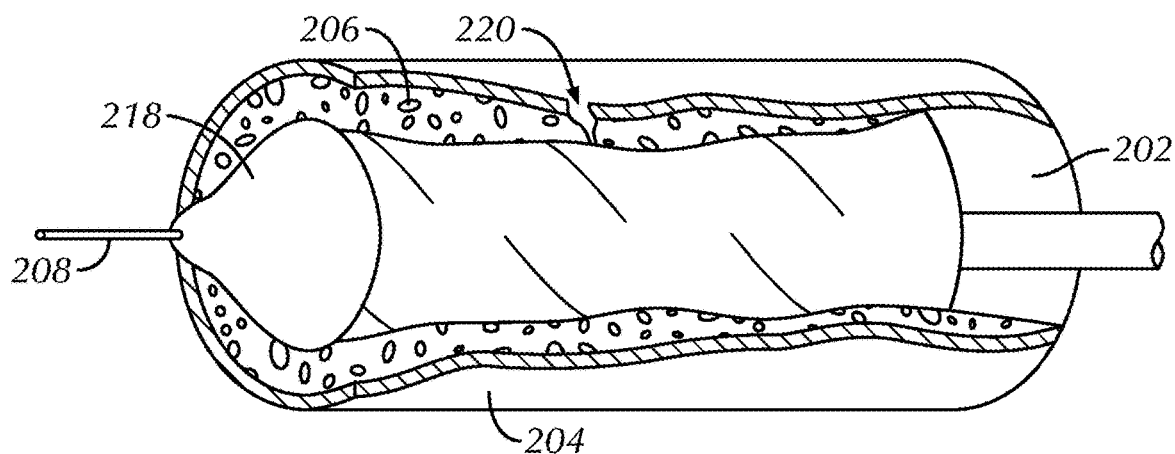
FIG. 2 illustrates a schematic view of a distal portion of a treatment device dilating an occlusion within a vessel segment, such dilation causing dissection of the vessel's wall.

FIGS. 1 and 2 provide examples of complications related to CTO angioplasty interventions in which the present perfusion catheters and related methods can be beneficial. In patient's suffering from a CTO, successful treatment of the occlusion can be challenging. A factor that can determine whether a treating clinician can successfully treat the occlusion is the clinician's ability to advance a guidewire from a first side of the occlusion to a second side of the occlusion. In some instances, such as when the natural lumen 102 of a blood vessel 104 is totally occluded by hard plaque 106 (e.g., calcified atherosclerotic plaque), the guidewire 108 cannot cross the occlusion and, in response to a continued proximally-applied pushing force 110, its distal portion 112 may deviate to, and perforate 114, an adjacent vessel wall 116, as shown in FIG. 1.

In other instances, such as when the occlusive material 206 is soft or where the occlusion has a tiny opening, the guidewire 208 can be forced through the occlusive material and allowed to remain within the natural lumen 202 of the blood vessel 204. A treatment device, such as a balloon catheter 218, can be guided over the guidewire 208 to the occlusion site where it can be used to carry out dilation treatment. Mechanical dilatation of the vessel 204 with the balloon catheter 218 can be associated with plaque fracture, intimal wall splitting, and localized medial dissection. Dissection 220, if it occurs, may propagate into the media and through the adventitia (the outermost layer of the vessel wall), resulting in another form of coronary perforation as shown in FIG. 2.

Perforations and dissections are serious complications for a catheterization laboratory because of their associated morbidity and mortality rates and, for this reason alone, their management and treatment is important and should be initiated quickly. A first step in management and treatment can be the placement of a balloon to seal the perforation or dissection. Prolonged balloon inflation may successfully seal the perforation or stop the propagation of the dissection and can provide time to prepare and implant a covered stent, if needed.

The present perfusion catheter 300 can be used in cases where there is a vessel perforation or dissection to be treated and further in cases where there is occlusive material to be dilated. The catheter 300 can be advanced through a guide catheter and directed through vasculature for treatment of the vessel wall injury using a guidewire and optionally a placement catheter. The perfusion catheter 300 can include a proximal manifold 324 for coupling with an inflation syringe, an elongate shaft 326, and a distal balloon 328 to seal the perforation or dissection or dilate the occlusive material.

The elongate shaft 326 can serve two primary purposes. First, the elongate shaft 326 can transmit forces applied by a clinician to either advance or retract the perfusion catheter 300, and specifically the balloon 328, during an angioplasty or sealing procedure. By manipulating the elongate shaft 326, the balloon 328 can be inserted into and passed through a guide catheter and out the distal portion of the guide catheter to a perforation or dissection to be sealed or an occlusion to be dilated. Second, the elongate shaft 326 includes a lumen 330 for providing inflation fluid to, or withdrawing inflation fluid from, the balloon 328. The lumen 330 of the elongate shaft 326 can be in fluid communication with the manifold 324, couplable to an inflation syringe, at its proximal portion 332, and it can be in fluid communication with the interior of the balloon 328 near its distal portion 334.

The elongate shaft 326 can be eccentrically attached to a proximal portion 336 of the balloon 328 and can extend proximally for clinician accessibility outside the guide catheter. The elongate shaft 326 can be attached to the balloon 328 by wrapping the balloon 328 about the shaft's intermediate 338 or distal 334 portions and affixing it thereto. In an example, the elongate shaft 326 is attached to the proximal portion 336 of the balloon 328 for a minimum of 5 mm.

Figure 3:
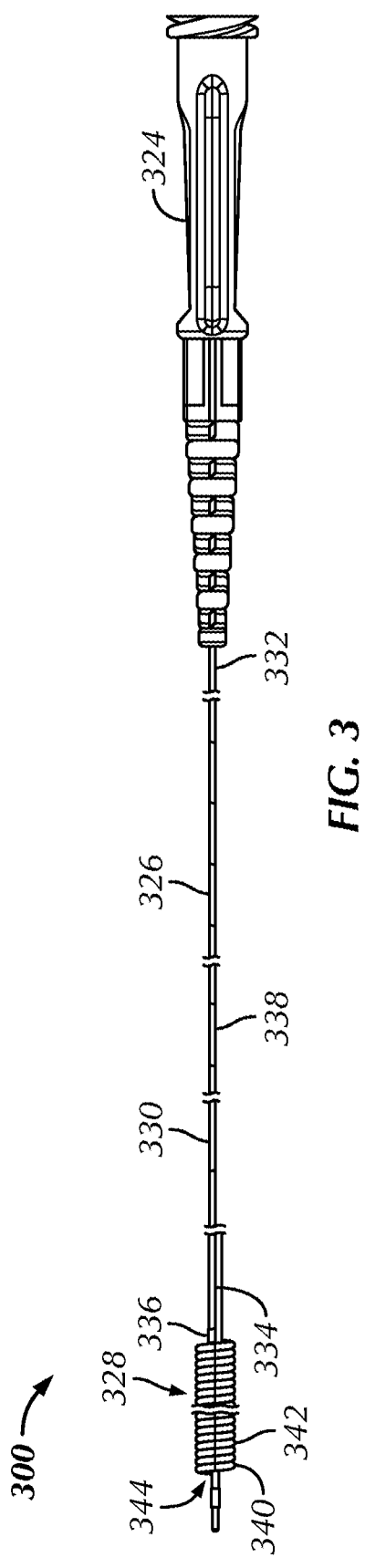
FIG. 3 illustrates a side view of a perfusion catheter, as constructed in accordance with at least one embodiment.

The embodiment of FIG. 3 illustrates that the balloon 328 can be formed from an inflatable tube 340 coiled in a helical or spiral manner around a central axis into a series of windings 342 (or loops), with consecutive or adjacent windings 342 stacked against and contacting each other with substantially no space therebetween. This can ensure the windings 342 act as a unit. The inner surfaces of the windings 342 can define a passage 344 through the open center of the helix when the coiled balloon 328 is inflated. The passage 344 can extend the full length of the balloon 328 to permit blood or other fluid to perfuse (or flow) therethrough, which is important since cutting off blood supply for extended periods of time is undesirable. When the balloon 328 is deflated, it can collapse or flatten into a low profile configuration, which may comprise one or more folds that wrap around the distal portion 334 of the elongate shaft 326. An elastic sheath can optionally be disposed around the balloon 328 and be utilized to reduce the collapsed profile of the deflated balloon so that it can be more easily inserted or removed from a patient.

Because the passage 344 is created by the balloon 328, blood flow is permitted through the passage 344 and the overall perfusion catheter 300 can be kept to a minimal size. This physical attribute allows the catheter 300 to be of a small diameter when it is inserted into the patient's body and maneuvered to the desired position, yet provides a relatively large blood flow passage when the balloon 328 is inflated.

Figure 4:
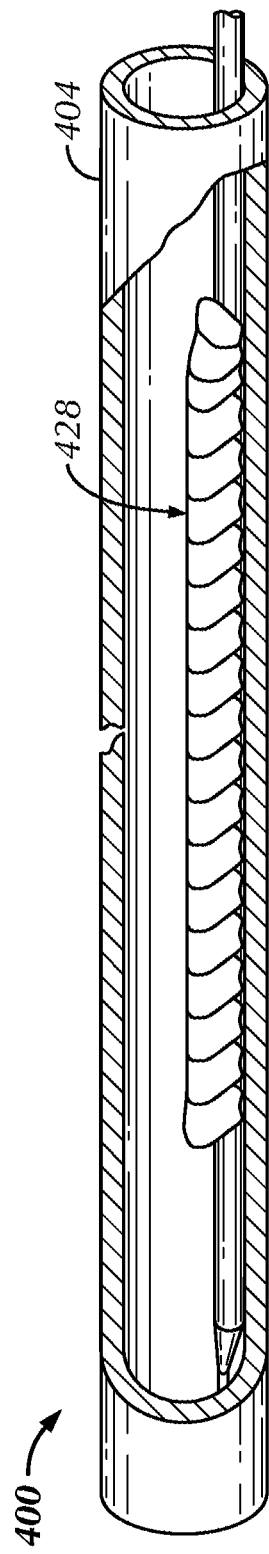
FIG. 4 illustrates an enlarged side view of a distal portion of the perfusion catheter shown in FIG. 3, with its balloon in a deflated configuration within a vessel segment.

FIG. 4 illustrates a perfusion catheter 400 in a blood vessel 404 of a patient. The catheter 400, and specifically a balloon 428 of the catheter, can be introduced and advanced within the blood vessel 404 in a low profile, unexpanded configuration. In this configuration, the balloon 428 is in a relaxed, folded, or crushed configuration and does not significantly increase the overall diameter of a distal portion of the catheter 400 such that it can be inserted into the patient and guided through the patient's vasculature to the desired treatment site.

Figure 5:
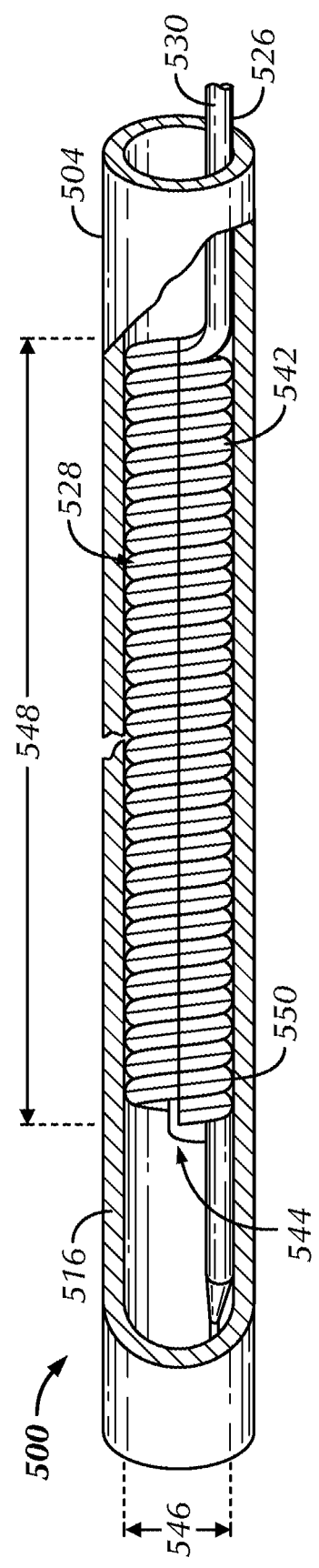
FIG. 5 illustrates an enlarged side view of a distal portion of the perfusion catheter shown in FIG. 3, with its balloon in an inflated configuration within a vessel segment.

Once at the treatment site, the balloon 528 can be inflated as illustrated in FIG. 5. Fluid under pressure can be supplied to the balloon 528 through an inflation lumen 530 of an elongate shaft 526, thereby expanding the balloon 528 toward a wall 516 of the blood vessel 504, such as for sealing, opening, or otherwise treating it. When inflated, the balloon 528 can impinge upon or engage the vessel wall 516 at the treatment site at pressures of 2 atm-20 atm, for example, yet blood can be allowed to flow through the passage 544 defined by the balloon's windings 542. Since the passage 544 created through the windings 542 is relatively large compared to the size of the vessel 504, the interruption of blood flow through the vessel is minimized and the perfusion catheter 500 is capable of prolonged inflation for temporary hemostasis in coronary perforations or dissections.

Beyond allowing for fluid flow, the passage 544 of the balloon 528 can be adapted to slidably receive a treatment device (e.g., a smaller diameter balloon catheter, stent catheter, guidewire support catheter, or guidewire). The balloon 528 can include any number of windings 542 in a number of sizes and configurations depending upon the particular treatment site, procedure and/or patient. Increasing the number of windings 542 in the balloon 528 can increase the ability of the balloon 528 to maintain a dilated state of an occlusion. The passage 544 can have a diameter 546 ranging from 2 mm-6 mm and can extend 10 mm-50 mm in length 548, for example. The diameter 546 of the passage 544 can be sufficiently large to permit entry of a stent catheter. The present inventors recognize that plaque has a tendency to return to its original form and restrict passage. This restenosis, if it occurs, can occur as quickly as a few minutes. The perfusion catheter 500 allows the stent catheter to be delivered through the catheter while the balloon 528 dilates the occlusion. In this way, there can be minimal time between occlusion dilation and placement of a stent. The diameter 546 of the passage 544 can be sufficiently large to receive a guidewire support catheter to help pre-dilate or otherwise establish a pilot opening through the occlusion, or to receive the distal portion of a retrograde guidewire that is funneled into the passage 544 as a result of engagement between an outer surface 550 of the balloon 528 and the vessel wall 516.

When the procedure is completed, the balloon 528 can be deflated by applying vacuum to a proximal manifold coupled with the inflation lumen 530 of the elongate shaft 526. The entire perfusion catheter 500 can then be removed.

Figure 6:
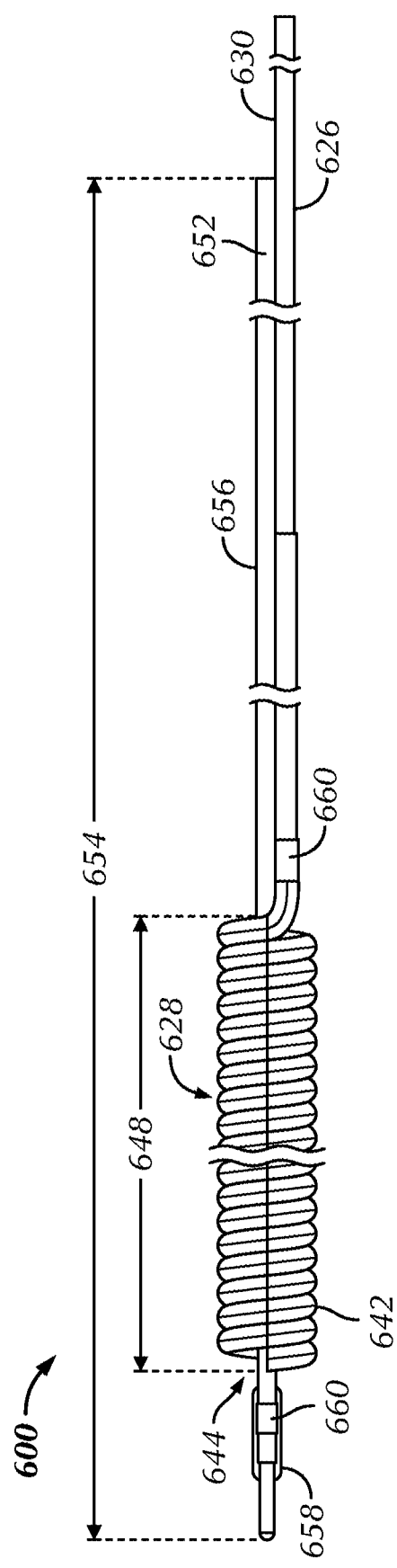
FIG. 6 illustrates an enlarged side view of a distal portion of a perfusion catheter including a dedicated guidewire lumen, as constructed in accordance with at least one embodiment.

FIG. 6 illustrates an enlarged side view of a distal portion of a perfusion catheter 600, as constructed in accordance with at least one embodiment. The catheter 600 can be provided with a guidewire lumen 652 separate from a passage 644 defined by windings 642 of a balloon 628 and separate from a lumen 630 of an elongate shaft 626 for providing inflation fluid to, or withdrawing inflation fluid from, the balloon 628. The guidewire lumen 652 can have a length 654 approximately equal to, or slightly longer than, the length 648 of the passage 644 and can be positioned therein. An outer surface of a guidewire support tube 656 forming the guidewire lumen 652 can contact inner surfaces of the windings 642 of the balloon 628 and can optionally be inset in these inner surfaces. Polymers of the guidewire support tube 656 and the balloon 628 can be configured to adhere to each other upon application of heat treatment.

The guidewire lumen 652 is designed to receive and facilitate tracking of a previously positioned guidewire having its distal portion in position near or across a treatment site. The perfusion catheter 600, and specifically the guidewire support tube 656, can be slid over the guidewire and advanced to the treatment site. An inner diameter of the guidewire support tube 656 can be sized to be advanced over a 0.36 mm (0.014 in) guidewire, for example. An atraumatic tip 658 can be disposed at a distal tip of the guidewire support tube 656 to prevent the perfusion catheter 600 from perforating a blood vessel during deployment and use. Since the guidewire support tube 656 can be short compared to the total lengths of the catheter 600 and the guidewire, the use of the guidewire support tube 656 as a guide permits rapid exchange of the catheter 600 over the guidewire.

One or more radiopaque markers 660 can be placed on the guidewire support tube 656 or the elongate shaft 626 proximal or distal to the balloon 628. These markers 660 can facilitate proper placement of the balloon 628 relative to a vessel wall injury prior to its inflation and can be any suitable radiopaque material detectable through the use of x-ray or fluoroscopy. Materials such as the platinum series of metals (e.g., platinum or palladium), gold, silver, iridium, or tantalum can be used as the markers. Certain stainless steels can also be suitable for use as markers. Alternatively, the polymer used in portions of the perfusion catheter 600 can be radiopaque or made so by addition of filler such as barium sulfate, bismuth trioxide, bismuth carbonate, tungsten, tantalum, or the like.

Figure 7:
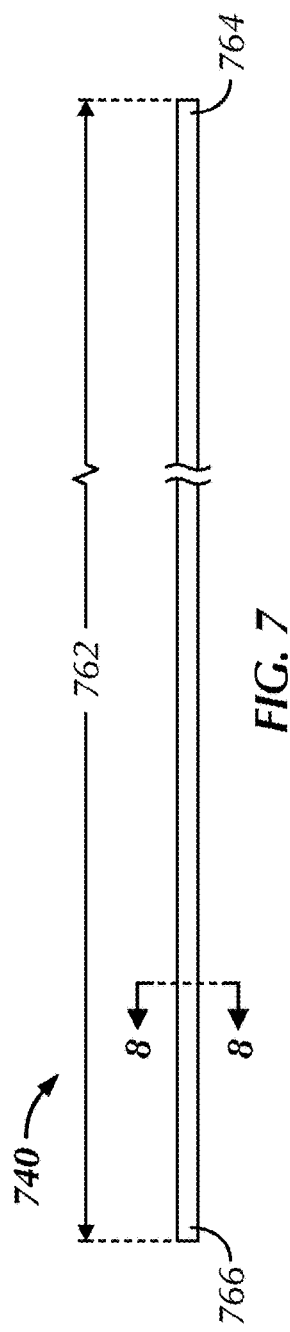
FIG. 7 illustrates a side view of extruded tubing for use in a balloon of a perfusion catheter, as constructed in accordance with at least one embodiment.
Figure 8:
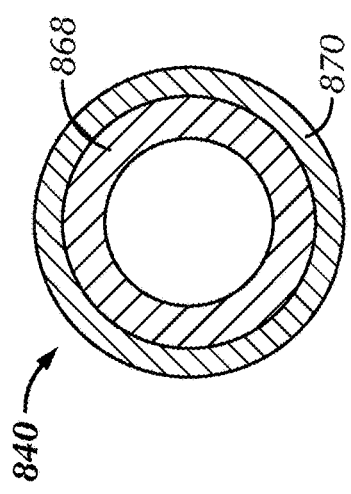
FIG. 8 illustrates a cross-sectional view of the extruded tubing shown in FIG. 7.

FIGS. 7 and 8 respectively illustrate side and cross-sectional views of extruded tubing 740 for use in a balloon of a perfusion catheter, as constructed in accordance with at least one embodiment. The extruded tubing 740 can have a uniform outer diameter along its length 762 or can have a larger diameter along a majority of its length and tapered down on its proximal 764 and distal 766 portions. The distal portion 766 of the extruded tubing 740 can be closed by crimping the tubing and/or plugging it with a thermoplastic filler or the like. The length 762 of the extruded tubing 740 can range from 40 cm-120 cm before being coiled in a helical or spiral manner into a series of windings.

The coiled shape of the balloon can be maintained by causing adjacent windings to adhere to one another and the integrity of the balloon can be internally provided within each winding. These qualities can be accomplished by coextruding a combination of nested polymers which, after winding of the coil, can be heat treated to allow adjacent coils to stick to each other. In the example of FIG. 8, the extruded tubing 840 is formed by coextruding two different polymer tubes 868, 870 (or layers), one slightly smaller than the other. The coextrusion process can eliminate seams, which are found in existing balloon designs, form tight bonds, and create a balloon using a reduced number of manufacturing steps. Alternatively, the smaller tube 868 can be inserted inside the larger tube 870 post-extrusion.

The smaller, inner tube 868 can be formed from a polymer having sufficient radial stiffness to resist collapse or bursting when exposed to inflation pressures, and the larger, outer tube 870 can be formed from a polymer configured to exhibit adhesive properties when heated and compliant properties when used within the body. The adhesive properties of the outer tube 870 can allow adjacent windings to adhere to one another. The use of a compliant material for the outer tube 870 can enable the balloon to conform to a vessel wall at the site of a perforation or tear, so that a substantial portion of the balloon's outer surface can be compressed against the vessel wall, or at the site of an occlusion that can benefit from being dilated. In various examples, the inner tube 868 can include polyethylene terephthalate (PET) or Pebax® polyether block amides (which are available from Arkema) having an outer diameter of 0.2 mm-0.28 mm and an inner diameter of 0.12 mm-0.18 mm, and the outer tube 870 can include Hytrel® polyester elastomer (which is available from E.I. du Pont de Nemours and Company), Pebax, or nylon having an outer diameter of 0.28 mm-0.36 mm and an inner diameter of 0.20 mm-0.28 mm. The inner 868 and outer 870 tubes can include polymers having different melting or softening temperatures, with the inner tube 868 including the polymer with the higher melting temperature. The inner 868 and outer 870 tubes can include the same or similar polymers, with the polymer of the inner tube 868 being cross-linked for strength and with the polymer of the outer tube 870 not being cross-linked.

Figure 9:
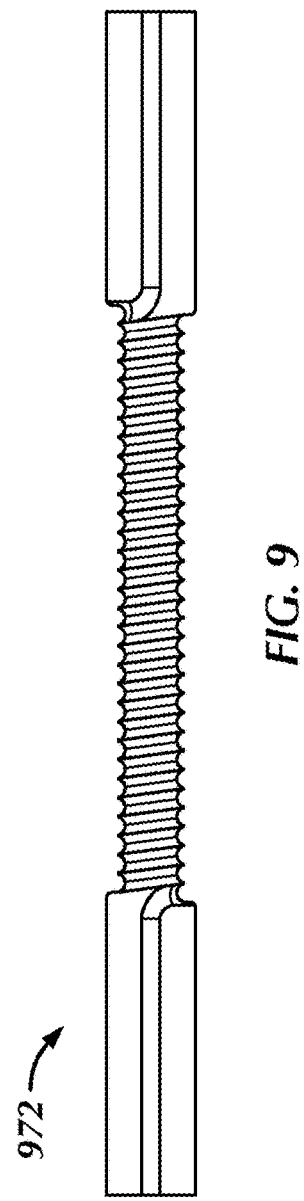
FIG. 9 illustrates a mandrel for manufacturing a balloon of a perfusion catheter, as constructed in accordance with at least one embodiment.

FIG. 9 illustrates a mandrel 972 for coiling extruded tubing in a helical manner around a central axis into a series of windings to form a balloon. The extruded tubing can be wrapped in a distal direction about the mandrel 972, which includes a shape of the intended profile of the balloon. After being wrapped onto the mandrel 972, the extruded tubing can be pressurized or inflated and adjacent windings can be heat set in order to ensure that they adhere to one another and the balloon maintains its coiled shape. For example, heat setting the coiled configuration of the balloon can include causing the outer surface of adjacent windings of the extruded tubing to adhere to one another via heating the tubing or the mandrel 972. The extruding tubing can then be cooled to room temperature.

Figure 10:
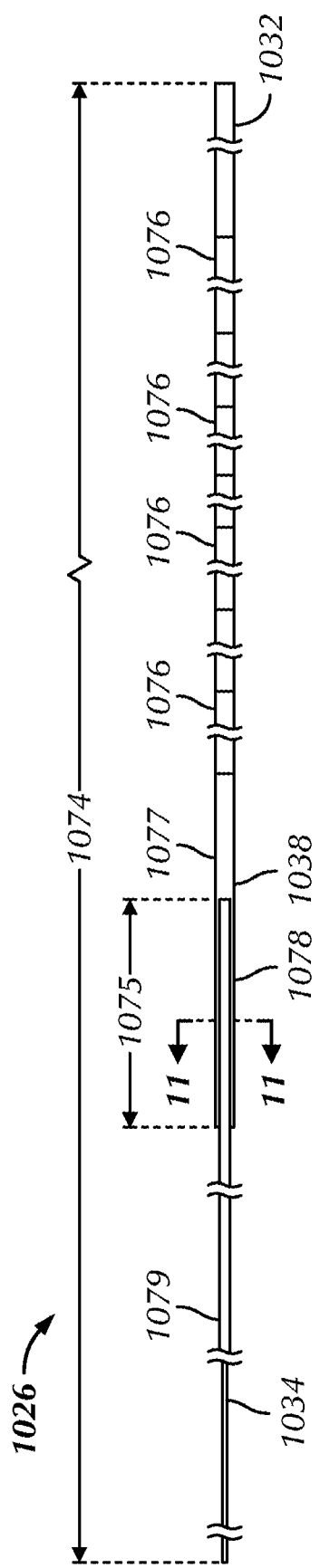
FIG. 10 illustrates a side view of an elongate shaft of a perfusion catheter, as constructed in accordance with at least one embodiment.
Figure 11:
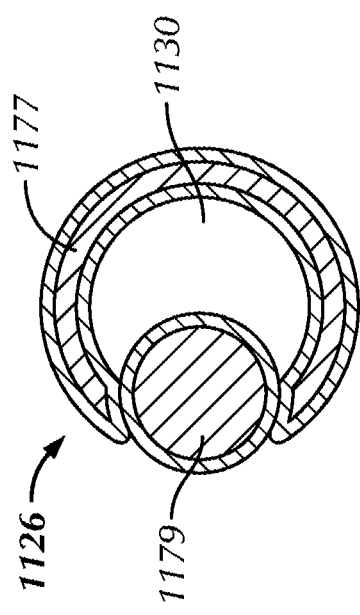
FIG. 11 illustrates a cross-sectional view of the elongate shaft shown in FIG. 10.

FIGS. 10 and 11 respectively illustrate side and cross-sectional views of an elongate shaft 1026, 1126 of a perfusion catheter, as constructed in accordance with at least one embodiment. The elongate shaft 1026, 1126 can include a lumen 1130 extending from a proximal portion 1032 to an inflation port for providing inflation fluid to, or withdrawing inflation fluid from, a distal balloon. The elongate shaft 1026, 1126 can extend a length 1074 of 100 cm-180 cm and can possess the qualities of compression rigidity along its longitudinal axis, which facilitates advancement of the perfusion catheter through a patient's vascular system, and good distal flexibility, which enhances maneuverability of catheter through directional changes of the vascular system and prevents damage to the vessel walls as it is being inserted. Portions of the elongate shaft 1026, 1126 can include a PTFE coating 1076 to facilitate its advancement through the patient's vascular system.

These qualities are achievable in a variety of ways. In an example, proximal 1032 and intermediate 1038 portions of the elongate shaft 1026, 1126 can include a stainless steel hypotube 1077, 1177, and the distal portion 1034 can include a stainless steel support wire 1079, 1179 or tube that is connected for a length 1075 to the intermediate portion. The support wire 1079, 1179 can help transmit forces applied by a treating clinician to either advance or retract the balloon during a treatment procedure. The support wire 1079, 1179 can range in length from 10 cm-20 cm and can be secured to the hypotube 1077, 1177 via a laser weld. The support wire 1079, 1179 can extend to a location distal to the balloon or can terminate between the balloon's proximal and distal portions. In another embodiment, the elongate shaft 1026, 1126 can be formed from a single piece of metallic or polymer tubing with a proximal portion that has an outer and inner diameter larger than an outer and inner diameter of a distal portion or with a proximal portion having greater wall thickness than a distal portion.

A means to affix an outer surface 1078 of the elongate shaft 1026, 1126 and the flexible material of the balloon can be employed to withstand stresses associated with pressure changes of inflation and deflation of the balloon. It can be important that the affixing means create a fluid tight seal between the two materials and restrict any delamination along the seal line during prolong periods of working pressures. In an example, portions of the elongate shaft 1026, 1126 coupled with the balloon can be covered with nylon (e.g., Vestamid L2101) as part of the affixing means. The materials can be joined by an adhesive process, such as a cyanoacrylate, epoxy or urethane compounds, or joined by a heat treatment or pressure fit process that melts or welds the two materials together.

Figure 12:
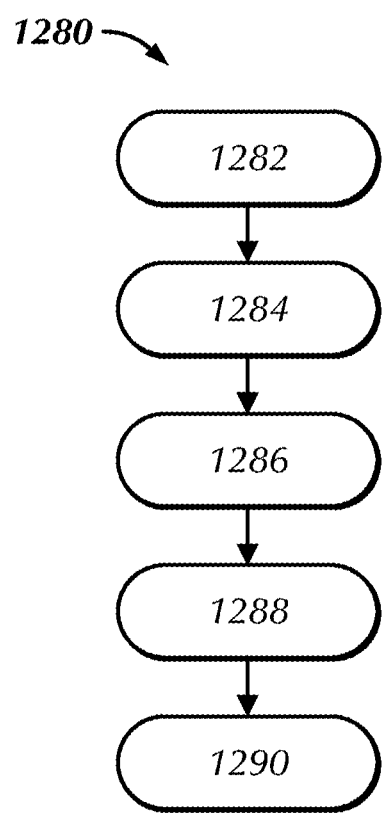
FIG. 12 illustrates a method of using a perfusion catheter for sealing a vessel perforation or dissection or dilating a vessel occlusion while maintaining a passage, as constructed in accordance with at least one embodiment.

FIG. 12 illustrates a method 1280 of using a perfusion catheter in a coronary vessel for sealing a perforation or dissection or dilating occlusive material while maintaining a passage.

At 1282, a guidewire can be introduced into a patient's blood system near the groin and advanced along the aorta, with the aid of a previously-placed guide catheter, to the selected coronary vessel for treatment. The guidewire can then be advanced to or across the treatment site desired for sealing or dilation. With the optional assistance of a placement catheter partially inflated and the perfusion catheter fully deflated, the catheter assembly can be threaded over the guidewire and advanced until its distal end is positioned near or within the treatment site, at 1284.

At 1286, a balloon of the perfusion catheter can be inflated from the fully deflated configuration to an expanded configuration by urging fluid through an elongate shaft. A lumen of the elongate shaft can be in fluid communication with a manifold, couplable to an inflation syringe, at its proximal portion, and it can be in fluid communication with the interior of the balloon near its distal portion. Upon expansion, an outer surface of the balloon can engage the wall of the coronary vessel, such as wall portions surrounding a vessel perforation or dissection or plaque accumulation on the wall, and the inner surface of the balloon can form a passage. The balloon can be inflated to pressures in the range of 2-20 atm, for example. These low pressures permit the balloon to be thin walled, e.g., 0.1-0.5 mm, thereby allowing a larger passage for blood flow. Additionally, low inflation pressures allow blood flow in the capillaries at the treatment site. The placement catheter, if used, can now be deflated and retracted proximally, allowing the perfusion of blood flow from a proximal arterial segment and through the passage to oxygenated myocardial tissues distal to the balloon and treatment site.

At 1288, a treatment device can optionally be passed at least partially through the guide catheter and the perfusion catheter. During the passage, the treatment device can be advanced along the elongate shaft, through the passage of the perfusion catheter to a target site in the coronary vessel.

At 1290, when sufficient time has passed to tack up a dissection, occlude a perforation, or dilate occlusive material and it is desired to remove the perfusion catheter from the patient, the placement catheter can be re-inserted into the passage and partially inflated to engage an inner surface of the balloon. The balloon of the perfusion catheter can then be deflated and the catheter assembly can be retracted and removed from the patient. In the alternative embodiment of a perfusion catheter including an independent guidewire lumen, the step of re-advancing the placement catheter can be eliminated. When it is desired to remove the perfusion catheter, the clinician can simply deflate the balloon to disengage it from the vessel wall, reducing the profile of the catheter and then, the perfusion catheter including the deflated balloon can be retracted along the guidewire.

Closing Notes:

Despite advances in the treatment of CTOs, certain complications still persist. Two of the most feared complications during CTO procedures are coronary perforation or dissection. The present perfusion catheters and related methods can be used in cases where there is a vessel perforation or dissection to be treated and further in cases where there is occlusive material to be dilated. The catheters and methods have several advantages over existing devices and techniques. First, the large diameter of the present catheter's passage can permit relatively high blood flow rates while the balloon is inflated. This allows for prolonged inflation of the balloon within a blood vessel to treat a perforation or dissection without blocking blood flow. Second, because the passage can be aligned with the primary flow axis of the vessel, there are fewer traumas to the blood and less pressure head required for blood flow. Third, the ability to maintain the position of the guidewire while permitting perfusion offers an important option to the clinician.

The above Detailed Description includes references to the accompanying drawings, which form a part of the Detailed Description. The Detailed Description should be read with reference to the drawings. The drawings show, by way of illustration, specific embodiments in which the present catheters and related methods can be practiced. These embodiments are also referred to herein as "examples."

The Detailed Description is intended to be illustrative and not restrictive. For example, the above-described examples (or one or more features or components thereof) can be used in combination with each other. Other embodiments can be used, such as by one of ordinary skill in the art upon reviewing the above Detailed Description. Also, various features or components have been or can be grouped together to streamline the disclosure. This should not be interpreted as intending that an unclaimed disclosed feature is essential to any claim. Rather, inventive subject matter can lie in less than all features of a particular disclosed embodiment. Thus, the following claim examples are hereby incorporated into the Detailed Description, with each example standing on its own as a separate embodiment:

In Example 1, a perfusion catheter can include a balloon including an inflatable tube and an elongate shaft including a lumen for providing inflation fluid to, or withdrawing inflation fluid from, the balloon. The inflatable tube can be coiled in a helical manner around a central axis into a series of windings. Adjacent windings can be stacked against and bonded to each other, and an inner surface of the series of windings, when inflated, can define a passage. The elongate shaft can be eccentrically attached to a proximal portion of the balloon and its lumen can be in fluid communication with the interior of the balloon, and specifically the inflatable tube.

In Example 2, the perfusion catheter of Example 1 can optionally be configured such that the inflatable tube includes two different polymer tubes.

In Example 3, the perfusion catheter of Example 2 can optionally be configured such that the two different polymer tubes include an inner tube and an outer tube. The inner tube is positioned within the outer tube.

In Example 4, the perfusion catheter of Example 3 can optionally be configured such that the polymer of the inner tube has a higher melting temperature than the polymer of the outer tube.

In Example 5, the perfusion catheter of any one or any combination of Example 3 and 4 can optionally be configured such that the polymer of the inner tube is cross-linked and the polymer of the outer tube is non-cross-linked.

In Example 6, the perfusion catheter of any one or any combination of Examples 2-5 can optionally be configured such that the two different polymer tubes are coextruded.

In Example 7, the perfusion catheter of any one or any combination of Examples 1-6 can optionally be configured such that the inflatable tube has a length ranging from 40 cm-120 cm before being coiled in the helical manner.

In Example 8, the perfusion catheter of any one or any combination of Examples 1-7 can optionally be configured such that the passage has a diameter ranging from 2 mm-6 mm and a length range from 10 mm-50 mm.

In Example 9, the perfusion catheter of any one or any combination of Examples 1-8 can optionally be configured such that the balloon is wrapped about a portion of the elongate shaft.

In Example 10, the perfusion catheter of Example 9 can optionally be configured such that the portion of the elongate shaft about which the balloon is wrapped is covered with nylon.

In Example 11, the perfusion catheter of any one or any combination of Examples 9 and 10 can optionally be configured such that the balloon is wrapped about the elongate shaft for a minimum of 5 mm.

In Example 12, the perfusion catheter of any one or any combination of Examples 1-11 can optionally be configured such that a proximal portion and an intermediate portion of the elongate shaft include a hypotube.

In Example 13, the perfusion catheter of Example 12 can optionally be configured such that a distal portion of the elongate shaft includes a support wire that is coupled to the intermediate portion.

In Example 14, the perfusion catheter of Example 13 can optionally be configured such that the support wire extends to a location distal to the balloon.

In Example 15, the perfusion catheter of any one or any combination of Examples 13 and 14 can optionally be configured such that the support wire extends to a location between a proximal portion and a distal portion of the balloon.

In Example 16, the perfusion catheter of any one or any combination of Examples 1-15 can optionally further comprise a guidewire lumen.

In Example 17, the perfusion catheter of Example 16 can optionally be configured such that the guidewire lumen is positioned within the passage.

In Example 18, the perfusion catheter of any one or any combination of Examples 16 and 17 can optionally be configured such that the guidewire lumen is inset into the inner surface of the series of windings.

In Example 19, the perfusion catheter of any one or any combination of Examples 16-18 can optionally be configured such that the guidewire lumen is equal to, or slightly longer than, a length of the passage.

In Example 20, the perfusion catheter of any one or any combination of Examples 1-19 can optionally further comprise a first radiopaque marker positioned proximal to the balloon and a second radiopaque marker positioned distal to the balloon.

In Example 21, a method can include inserting a guidewire into a blood vessel and advancing the guidewire to or across a treatment site, passing a perfusion catheter over the guidewire until a distal portion of the perfusion catheter is positioned near or within the treatment site, and inflating a balloon of the perfusion catheter. Inflating the balloon can include inflating a series of contacting windings of helically-wound tubing. The balloon, upon inflation, can move from a deflated configuration to an inflation configuration at which an outer surface of the balloon can engage a wall of the blood vessel and an inner surface of the balloon can define a passage.

In Example 22, the method of Example 21 can optionally be configured such that inflating the balloon includes allowing a flow of bodily fluid through the passage.

In Example 23, the method of Example 21 can optionally be configured such that inflating the balloon includes sealing a perforation in the wall of the blood vessel while allowing a flow of bodily fluid through the passage.

In Example 24, the method of Example 21 can optionally be configured such that inflating the balloon includes expanding an occluded or narrowed region in the blood vessel.

In Example 25, the method of any one or any combination of Examples 21-24 can optionally further comprise passing a treatment device at least partially through the passage.

In Example 26, the method of Example 25 can optionally be configured such that passing the treatment device at least partially through the passage includes receiving, in a distal-to-proximal direction, a treatment device that is funneled into the passage as a result of the engagement between the outer surface of the inflated balloon and the wall of the blood vessel.

In Example 27, the method of Example 25 can optionally be configured such that passing the treatment device at least partially through the passage includes delivering, in a proximal-to-distal, a treatment device to the treatment site or distal to the treatment site.

In Example 28, the method of any one or any combination of Examples 21-27 can optionally further comprise deflating the balloon and withdrawing the perfusion catheter from the blood vessel.

In Example 29, the perfusion catheter or method of any one or any combination of Examples 1-28 can optionally be configured such that all components or options recited are available to use or select from.

Certain terms are used throughout this patent document to refer to particular features or components. As one skilled in the art will appreciate, different persons may refer to the same feature or component by different names. This patent document does not intend to distinguish between components or features that differ in name but not in function.

For the following defined terms, certain definitions shall be applied unless a different definition is given elsewhere in this patent document. The terms "a," "an," and "the" are used to include one or more than one, independent of any other instances or usages of "at least one" or "one or more." The term "or" is used to refer to a nonexclusive or, such that "A or B" includes "A but not B," "B but not A," and "A and B." The terms "distal" and "proximal" are used to refer to a position or direction relative to a treating clinician. "Distal" or "distally" refer to a position that is further from the treating clinician. "Proximal" and "proximally" refer to a position that is closer to the treating clinician. The term "patient" refers to a human patient or an animal patient. The terms "clinician" or "treating clinician" refer to a doctor, nurse or other care provider and can include support personnel. The term "occlusion" refers to a total, near total or partial blockage of a blood vessel.

The scope of the invention should be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended; that is, a device, kit or method that includes features or components in addition to those listed after such a term in a claim are still deemed to fall within the scope of that claim. Moreover, in the following claims, the terms "first," "second" and "third," etc. are used merely as labels, and are not intended to impose numerical requirements on their objects. It is to be understood that although the dependent claims may be set out in single dependent form, the features of these claims can be combined as if the claims were in multiple dependent form.

The Abstract is provided to allow the reader to quickly ascertain the nature of the technical disclosure. It is submitted with the understanding that it will not be used to interpret or limit the scope or meaning of the claims.

What is claimed is:

1. A perfusion catheter, comprising:
   a balloon including an inflatable tube coiled in a helical manner around a central axis into a
   series of windings with adjacent windings stacked against and bonded to each other, an inner surface of the series of windings, when inflated, defining a passage through the center of the helix for delivery of a medical device or maintaining blood flow; an elongate shaft extending proximal of the balloon and eccentrically positioned relative to the passage; and
   a guidewire support tube having a length less than a combined length of the balloon and the elongate shaft and having a guidewire lumen therethrough, the guidewire support tube extending through the passage, inset in the interior surface of the series of windings, and non-coaxial with the elongate shaft.

2. The perfusion catheter of claim 1, wherein the inflatable tube of the balloon includes two different polymer tubes, an inner tube positioned within an outer tube, that are coextruded.

3. The perfusion catheter of claim 2, wherein the inner tube is formed from a polymer having a radial stiffness to resist collapse or bursting when exposed to inflation pressures, and the outer tube is formed from a polymer configured to exhibit adhesive properties when heated.

4. The perfusion catheter of claim 2, wherein the inner tube is formed from a polymer that is cross-linked, and the outer tube is formed from a polymer that is non-cross-linked.

5. The perfusion catheter of claim 2, wherein the inner tube is formed from a polymer having a higher melting temperature than a polymer that forms the outer tube.

6. The perfusion catheter of claim 1, wherein a proximal portion of the elongate shaft includes a hypotube.

7. The perfusion catheter of claim 6, wherein a distal portion of the elongate shaft includes a support wire that is coupled to the hypotube.

8. The perfusion catheter of claim 7, wherein the support wire extends to a location distal to the balloon.

9. The perfusion catheter of claim 1, wherein a proximal end of the balloon is wrapped about a portion of the elongate shaft.

10. The perfusion catheter of claim 9, further comprising means to affix the elongate shaft and the proximal end of the balloon, the means to affix creating a fluid tight seal between the elongate shaft and the balloon.

11. The perfusion catheter of claim 10, wherein the means to affix includes nylon.

12. The perfusion catheter of claim 1, wherein a polymer of the guidewire support tube and a polymer of the inflatable tube are configured to adhere to each other upon application of heat treatment.

13. The perfusion catheter of claim 1, wherein the length of the guidewire support tube is longer than a length of the passage.

14. The perfusion catheter of claim 1, wherein a distal tip of the guidewire support tube includes an atraumatic tip.

15. The perfusion catheter of claim 1, further comprising a first radiopaque marker positioned proximal to the balloon and a second radiopaque marker positioned distal to the balloon.

16. The perfusion catheter of claim 1, further comprising a first radiopaque marker positioned on the elongate shaft and a second radiopaque marker position on the guidewire support tube.

17. The perfusion catheter of claim 1, wherein the passage has a diameter ranging from 2 mm-6 mm and a length ranging from 10 mm-50 mm.

18. The perfusion catheter of claim 1, wherein the balloon, when inflated, impinges upon or engages a vessel wall at a treatment site at pressures of 2 atm-20 atm.

19. The perfusion catheter of claim 1, further comprising an elastic sheath disposed around the balloon.

* * * * *